(12) United States Patent
Müller et al.

(10) Patent No.: US 8,657,494 B2
(45) Date of Patent: Feb. 25, 2014

(54) SWIVELING DEVICE FOR A SWIVELING C-ARM OF AN X-RAY UNIT

(75) Inventors: Klaus Müller, Knittlingen (DE); Willi Weisert, Oberderdingen (DE)

(73) Assignee: Richard Wolf GmbH, Knittlingen (DE)

( * ) Notice: Subject to any disclaimer, the term of this patent is extended or adjusted under 35 U.S.C. 154(b) by 387 days.

(21) Appl. No.: 13/012,247

(22) Filed: Jan. 24, 2011

(65) Prior Publication Data
US 2011/0179895 A1 Jul. 28, 2011

(30) Foreign Application Priority Data
Jan. 27, 2010 (DE) .................. 10 2010 005 787

(51) Int. Cl.
*F16H 19/02* (2006.01)
*F16H 19/06* (2006.01)

(52) U.S. Cl.
USPC ........... 378/204; 378/189; 378/193; 378/197; 74/29; 74/25; 74/37

(58) Field of Classification Search
None
See application file for complete search history.

(56) References Cited

U.S. PATENT DOCUMENTS

| | | | | |
|---|---|---|---|---|
| 4,955,046 A | * | 9/1990 | Siczek et al. | 378/197 |
| 4,979,202 A | * | 12/1990 | Siczek et al. | 378/198 |
| 4,987,585 A | * | 1/1991 | Kidd et al. | 378/197 |
| 5,226,069 A | | 7/1993 | Narita | |
| 6,113,265 A | * | 9/2000 | Babler | 378/197 |
| 6,364,525 B1 | * | 4/2002 | Mellstrom et al. | 378/197 |
| 6,374,937 B1 | * | 4/2002 | Galando et al. | 180/211 |
| 6,652,108 B1 | * | 11/2003 | Schillegger | 359/877 |
| 7,059,463 B2 | * | 6/2006 | Simmons | 192/95 |
| 2004/0015077 A1 | * | 1/2004 | Sati et al. | 600/427 |
| 2006/0098786 A1 | * | 5/2006 | Eck | 378/163 |
| 2008/0069309 A1 | * | 3/2008 | Dorre | 378/197 |

FOREIGN PATENT DOCUMENTS

| | | |
|---|---|---|
| DE | 100 43 473 A1 | 11/2001 |
| DE | 10 2008 019 345 A1 | 10/2009 |
| JP | 57-011637 A | 1/1982 |
| JP | 62-066598 A | 3/1987 |
| JP | 62-167536 A | 7/1987 |
| JP | 04-208137 A | 7/1992 |
| JP | 08-132936 A | 5/1996 |
| JP | 09-010193 A | 1/1997 |
| JP | 10-122259 A | 5/1998 |
| JP | 2002-238882 A | 8/2002 |

OTHER PUBLICATIONS

Office Action issued Aug. 14, 2012 in JP Application No. 2011-015288.
Office Action Issued Oct. 26, 2010 in German Appln. Ser. No. 10 2010 005 787.8.

* cited by examiner

*Primary Examiner* — Hoon Song
*Assistant Examiner* — Danielle Fox
(74) *Attorney, Agent, or Firm* — Panitch Schwarze Belisario & Nadel LLP

(57) ABSTRACT

A swiveling device for a swiveling C-arm of an X-ray unit includes a motorized drive unit and an adapter removably attachable to the C-arm concentrically with a swiveling axis thereof. The adapter connects the C-arm to the drive unit in driving manner. The swiveling device also includes an angular position encoder for recording the swivel angle of the C-arm.

9 Claims, 4 Drawing Sheets

SWIVELING DEVICE FOR A SWIVELING C-ARM OF AN X-RAY UNIT

BACKGROUND OF THE INVENTION

The present invention relates generally to a swiveling device for a swiveling C-arm of an X-ray unit.

Diagnostic X-ray units are used in conjunction with treatment devices to determine the treatment site inside the body precisely before treatment begins, and during treatment as necessary. For example, they are used in the extracorporeal treatment of concretions such as kidney and urinary calculus. In such procedures, the focus of the ultrasonic source to be used to disintegrate the concretion is aligned precisely with the treatment site that has been determined previously with the aid of the X-ray unit. To determine the treatment site, the patient who is to undergo the treatment is first roentgenized with the X-ray unit in two different planes. To do this, an X-ray unit C-arm is used, on which an X-ray source and an image amplifier are arranged directly opposite one another, and typically constructed in swiveling manner. Thus, the patient may be roentgenized, for example, first in a vertical plane and then, by swiveling the C-arm manually in a plane at an angle to the vertical plane, thereby providing the treatment site at the intersection of the ray paths in these two planes.

The precise adjustment of the C-arm when determined the treatment site is relatively complicated and requires a certain dexterity. This applies particularly if the C-arm, which should really not be moved out of position after the ultrasound source has been focused on the treatment site, is shifted inadvertently, or deliberately for reasons of the treatment, and has to be swiveled back to its original position again.

Against the above background, an objective of the present invention is to provide a device that enables the C-arm to be adjusted more precisely and with which it is easier to adjust a swiveling X-ray unit C-arm.

BRIEF SUMMARY OF THE INVENTION

The above objective is solved with a swiveling device having the features described in the independent claim(s) of the present application. Advantageous refinements of this swiveling device will be evident from a reading of the subordinate claims, the following description, and the drawing. Hereby, according to a preferred embodiment of the present invention, the features specified listed in the subordinate claims may furnish solution according to the independent claim(s) on their own or also in any combination.

The swiveling device according to a preferred embodiment of the present invention for a preferably laterally swiveling C-arm of an X-ray unit includes a motorized drive unit as well as an adapter that is attached to the C-arm concentrically with the swiveling axis thereof. The adapter may be used to connect the C-arm to the drive unit in driving manner, that is to say the drive unit may be connected to the C-arm via the adapter in such manner that the motion of a motorized drive of the drive unit, which is preferably realized as a rotary drive, may be transferred to the C-arm. In this case, it is expedient if the drive unit is mounted to a part of the X-ray unit that is constructed in fixed manner, unlike the C-arm, so that the C-arm is able to swivel relative to this part. The drive may be a direct drive, in which the rotating motion of the drive shaft of a drive motor is transferred directly to the C-arm. However, the torque required to swivel the C-arm is preferably transferred to C-arm via a gearbox fitted ahead of the C-arm, wherein a gearbox that reduces the rotating speed of the drive motor enables particularly precise angular positioning of the C-arm.

An angular position encoder or rotary angle detector is provided in the swiveling device according to the invention to record the exact swiveling angle of the C-arm, which may particularly be in an angular range of at least 60° and may preferably be in an angular range of at least 30° in two opposing directions about and with reference to a vertical normal position of the C-arm. This angular position encoder is connected by a signal to at least one device for displaying angles. A means for connecting the angular position encoder to a control device via a signal may also be provided, wherein the controller device may advantageously also include the angle display and may be used to actuate the drive unit. The angular position encoder may preferably record the angular position of the C-arm continuously while the C-arm is swiveling, so that an operator of an X-ray unit equipped with a swiveling device according to the invention may be aware of the current angular position of the C-arm at all times. This is particularly advantageous if the C-arm has already been aligned with the application site and is moved inadvertently, in which case it may be adjusted accordingly to realign it with the treatment site very easily because its former angular position is known precisely. In this context, it is also possible to have the drive unit actuated correspondingly via a control device connected to the angular position encoder if necessary, so that the C-arm may be moved back into the required position practically automatically by the drive unit.

The angular position encoder may be a sensor of such kind with which for example the angular position of the C-arm may be determined directly and without contact. However, it is preferably intended to use an angular position encoder that is arranged so as to record the angle of rotation of a part of the drive unit that may be connected to the adapter. This is advantageous in that the angular position encoder may then be disposed in a housing of the drive unit for protection.

The part of the drive unit that is connectable to the adapter is preferably connected directly to the adapter attached to the C-arm, so that the angle of rotation of this part matches the angle of rotation of the C-arm. In theory, the angular position encoder may be of any type, provided it can be used to determine rotational angle positions or at least changes in rotational angles of the part connected to the adapter. Thus, the angular position encoder used may be a sensor that captures the angular position or angular change by digital or analogue means, and in absolute or relative terms. A potentiometer having a slider or sliding contact which is kinetically coupled to the part of the drive unit that may be connected to the adapter is preferably used as the rotary angle detector. A belt drive is preferably provided to assure kinetic coupling of the slider with the part of the drive unit that may be connected to the adapter. A toothed belt drive is particularly suitable for use as the belt drive. Alternatively, it may also be advantageous to couple the slider kinetically to the part of the drive unit that may be connected to the adapter using a toothed wheel connection.

In a further advantageous embodiment, the drive shaft of the motorized drive of the drive unit in the swiveling device according to the present invention, which is preferably the drive shaft of an electric motor, may be coupled to the part of the drive unit that may be connected to the adapter in a joining manner via a worm drive. If a worm drive is used, it is possible to align the axis of rotation of the motor drive shaft and the axis of rotation of the part of the drive unit that may be connected to the adapter normally relative to one another so that the drive unit may be constructed in relatively compact manner. Moreover, it is possible to achieve quite large speed reductions with a worm drive, which in turn enables particularly good positional accuracy of the C-arm.

To enable torque to be transmitted reliably from the drive unit to the C-arm, the part of the drive unit that may be connected to the adapter may advantageously be furnished with positive locking elements, which are provided to engage in corresponding positive locking elements on the adapter. Conversely, it is generally also possible for positive locking elements to be conformed on the adapter, which may then be brought into engagement with the corresponding positive locking elements on the drive unit. The positive locking elements conformed on the drive unit and the adapter are typically constructed such that they form at least one positive locking connection of the adapter with the part of drive unit part that is connectable therewith perpendicularly to the direction of rotation of the latter part.

In an further advantageous design of the swiveling device according to the present invention, it may also be constructed so as to enable the C-arm to be swiveled rapidly by hand, thereby improving access to the treatment site. To this end, a friction clutch may be provided and arranged between the drive unit of the drive motor and the adapter. This friction clutch enables the drive train of the drive unit between the adapter and the drive motor to be disengaged temporarily by swiveling the C-arm manually. The part that may be connected to the adapter preferably forms a part of the friction clutch for this purpose.

In order to be able to use an X-ray unit without using the swiveling device according to the present invention in cases where the C-arm does not need to be adjusted so precisely, the adapter may be detached so that the drive unit may expediently be moved to a position where it does not obstruct the X-ray unit operator. For this purpose, the drive unit may be arranged on a pivot arm attached to the X-ray unit so that it may be swiveled away from the C-arm when necessary. On X-ray units equipped with a C-arm that is attached in height in adjustable manner to a vertically extensible mounting column provided on the X-ray unit, the pivot arm that supports the drive unit may expediently be mounted to this mounting column or to a component that travels with the mounting column, so that the drive unit may be connected to the adapter that is attached to the C-arm, regardless of the height at which the C-arm is set.

The adapter may preferably be attached to the C-arm by means of a clamping device. This clamping device is preferably constructed in such manner that the adapter is able to be attached to C-arms having various cross-sectional dimensions. In this way, it is possible for the swiveling device according to the invention to be used with a wide range of X-ray units made by various manufacturers. A clip with an opening on one side and the adapter arranged thereon may advantageously be provided as the clamping device, wherein the adapter is clamped to the C-arm and in a position enclosing it by suitable clamping means. With this clamping device, the width of the space enclosed by the clip is the only factor limiting the types of C-arm to which the clamping device can be attached.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
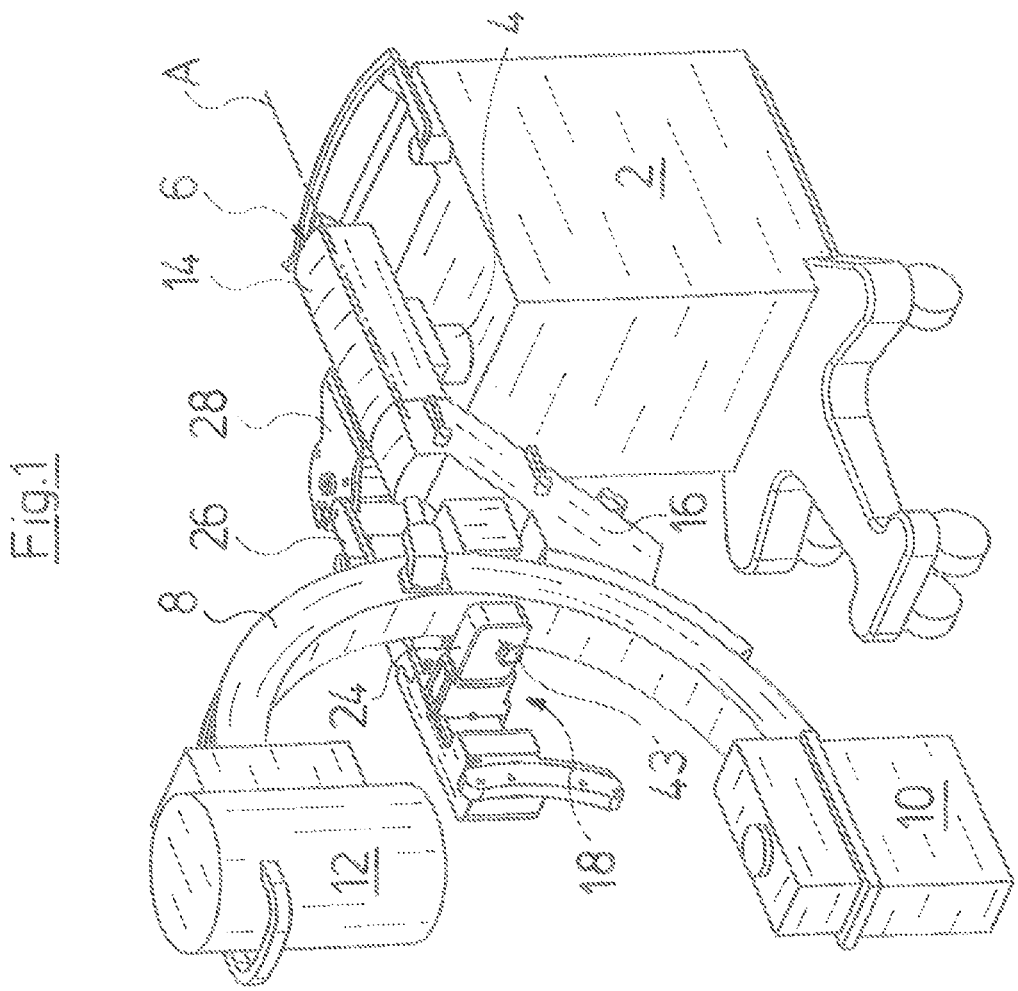
FIG. 1 is a perspective diagrammatic representation of an X-ray unit with a C-arm and a swiveling device for swiveling the C-arm according to a preferred embodiment of the present invention.

Certain terminology is used in the following description for convenience only and is not limiting. The words "bottom" and "top" designate directions in the drawings to which reference is made. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, the X-ray unit shown in FIG. 1 is a known device having an base cart 2, from the top of which an extendable mounting column 4 protrudes vertically. A C-arm 8 of the X-ray unit is attached in height-adjustable manner to mounting column 4 via an angled arm 6. An X-ray source 10 is attached to the bottom end of C-arm 8, and an image amplifier 12 is arranged at the bottom end thereof, both in the usual manner.

Figure 2:
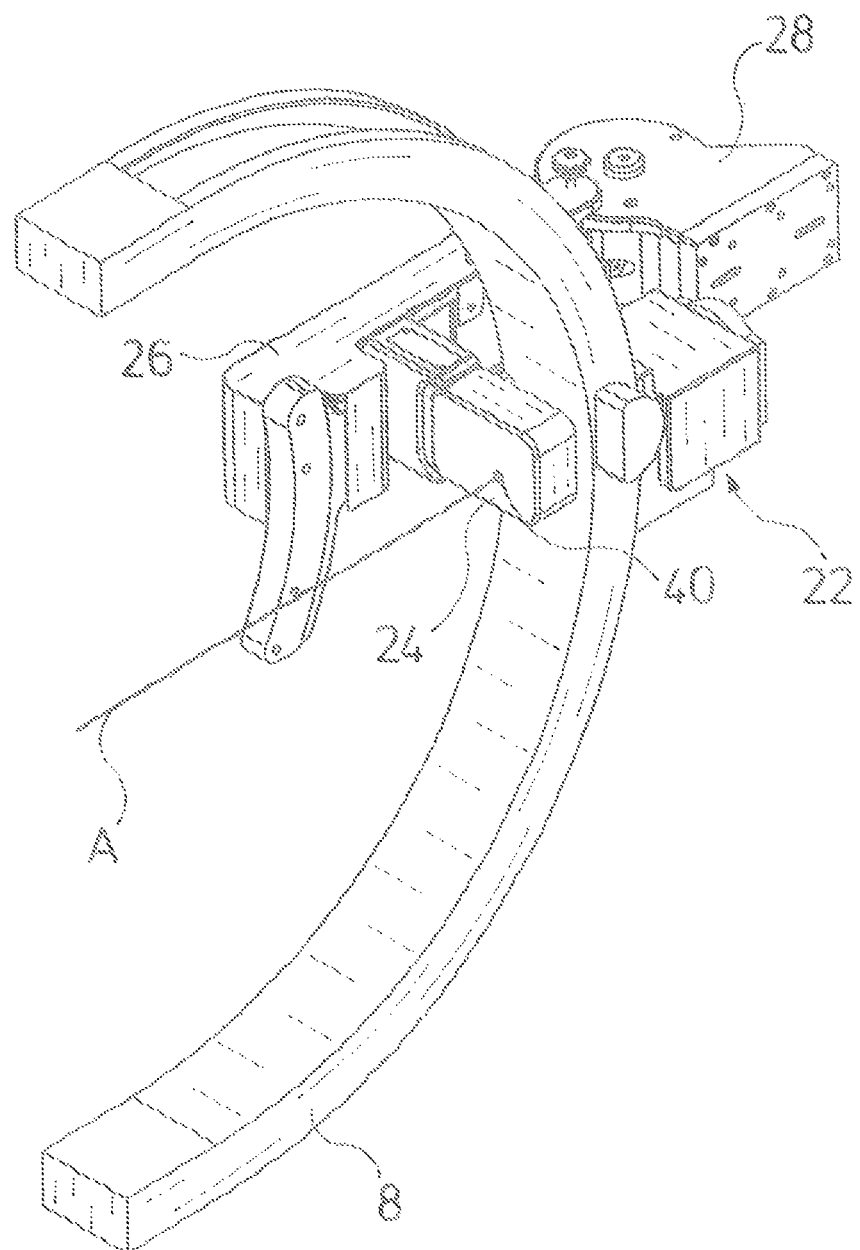
FIG. 2 is an enlarged perspective view of the C-arm and the swiveling device of the X-ray unit of FIG. 1 attached thereto.

Arm 6, to which C-arm 8 is secured, is of two-part construction and has a one arm segment 14 aligned normally with the lengthwise extension of mounting column 6, and one arm segment 16 extending downwards and at an angle to the first arm segment. Arm segment 16 is attached in articulated manner to arm segment 14 so as to swivel about a longitudinal axis A of arm segment 14. Thus, since C-arm 8 is attached to arm segment 16, it too is able to swivel about a longitudinal axis A of arm segment 14. Accordingly, the longitudinal axis A also forms a pivoting axis A of C-arm 8. A swiveling device 18, the construction and mode of operation of which is shown clearly in FIGS. 2-4, is provided for swiveling C-arm 8, and will be explained in greater detail in the following with reference to those figures.

Figure 3:
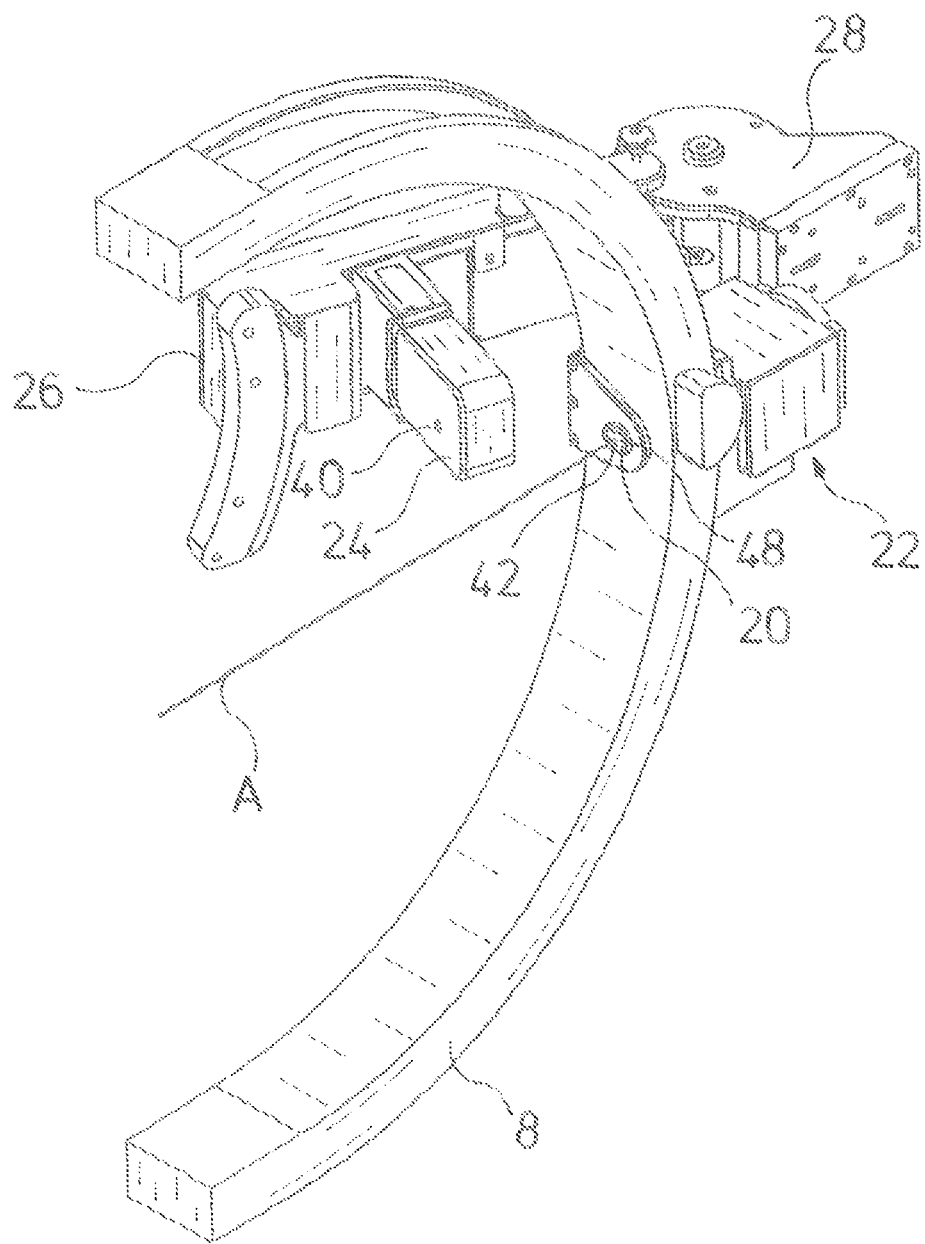
FIG. 3 shows the C-arm of FIG. 2 but with the swiveling device drive unit removed from the pivot arm.
Figure 4:
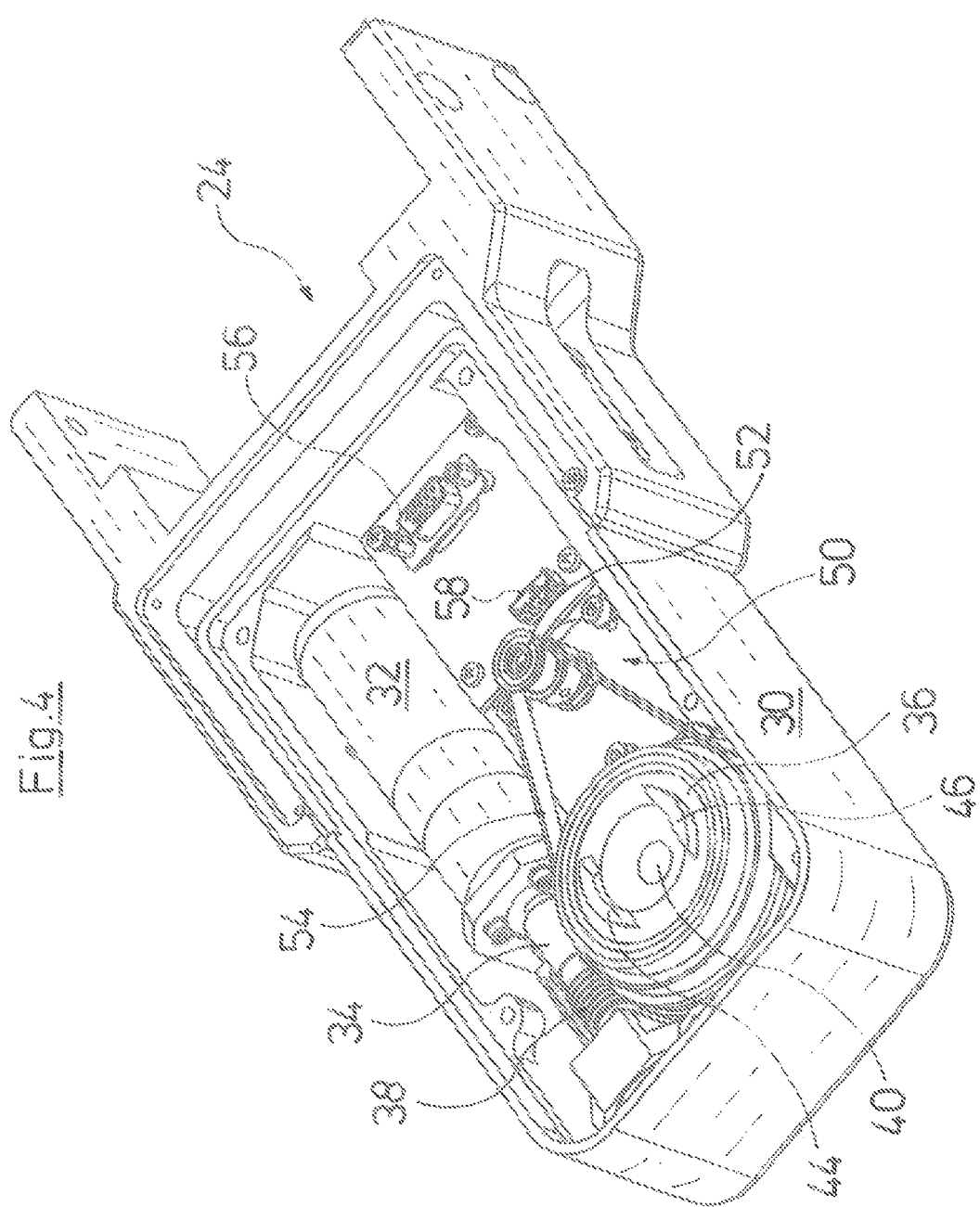
FIG. 4 is an enlarged diagrammatic representation of a drive unit of the swiveling device of FIGS. 1-3 with a housing open.

Swiveling device 18 is equipped with an adapter 20 (FIG. 3). This adapter 20 is a part of a clip-like clamping component 22 that is attachable to C-arm 8 of the X-ray unit, wherein it encloses C-arm 8 in such manner that adapter 20 is disposed on the concave side of arm 6 facing away from C-arm 8 and concentrically with longitudinal axis A, which is also the pivot axis of C-arm 8. Adapter 20 assures that C-arm 8 is kinetically coupled with a drive unit 24 of the swiveling device 18.

Drive unit 24 is attached to a pivot arm 26, which is attached in articulated manner to a longitudinal side of arm segment 14 of the X-ray unit via a joint 28. In this manner, drive unit 24 is adjustable in terms of height together with the C-arm. When pivot arm 26 is swiveled, drive unit 24 may be brought into a position in which C-arm 8 is connected to drive unit 24 in driving manner via adapter 20 (FIG. 2), and into a position in which the driving connection between C-arm 8 and drive unit 24 is disengaged (FIG. 3).

Drive unit 24 has an essentially rectangular housing 30, which is attached to pivot arm 26 in such manner that housing 30 extends traversely to the longitudinal extension of pivot arm 26. An electric motor 32 is located in housing 30 for drive unit 24. The electric motor 32 is disposed inside housing 30 in such manner that drive shaft 34 of the electric motor 32 extends in the lengthwise direction of housing 32.

The electric motor 32, which may be actuated by a controller (not shown) in such manner that its drive shaft 34 is rotatable in two opposite directions, is used to drive a drive wheel 36 that may be connected to adapter 20 and transfers a rotary motion of the drive shaft 34 of electric motor 32 to C-arm 8. The drive wheel 36 is supported inside housing 30 in such manner that its axis of rotation is aligned normally to and at a distance from the longitudinal extension of drive shaft 34 of electric motor 32. A worm drive is provided to transfer the rotary movement of drive shaft 34 to drive wheel 36. The worm drive has an endless screw 38 arranged on the drive shaft 34 of electric motor 32, which screw 38 is engaged by a worm gear, located below and rotationally coupled with drive wheel 36, and not shown in FIG. 4.

The drive wheel 36 has a central borehole 40 for attaching drive unit 24 to adapter 20, which borehole 40 also extends through the wall of housing 30 and opens onto the outer side of housing 30 facing away from the C-arm 8. The adapter 20 is also furnished with a borehole 42 corresponding to borehole 40 and aligned concentrically with longitudinal axis A. The boreholes 40 and 42 accommodate a screw 43, which connects drive unit 24 to adapter 20. The screw 43 is preferably furnished with a star knob so that drive unit 24 and adapter 20 may be connected or disconnected quickly by hand.

In order to enable a reliable transfer of torque from drive wheel 36 to adapter 20, drive wheel 36 forms a positive locking connection with adapter 20 when drive unit 24 is attached to adapter 20. For this purpose, drive wheel 36 is furnished with two projections 44 and 46 in the form of ring segments located opposite and at a distance from one another, which encompass a projection 48 conformed on adapter 20 when drive wheel 36 is disposed on the adapter 20.

FIG. 4 does not show that drive wheel 36 is part of friction clutch arranged between the worm drive and adapter 20, and is thus able to disengage from the rest of the drive train of drive unit 24 when a certain torque is exerted on drive wheel 36. This enables the swiveling C-arm 8 to be swiveled by hand as well if necessary, though it is otherwise swiveled by drive unit 24.

The swiveling device is equipped with an angular position encoder 50 so that the swiveling position of the C-arm may be determined with complete accuracy and reliability. This angular position encoder is used to record the rotational position of drive wheel 36 and thus also to record the swivel angle of C-arm 8, which is kinetically coupled to drive wheel 36. The angular position encoder is a potentiometer 50 that is located in housing 30 of drive unit 24. The potentiometer 50 is equipped with a shaft 52, which is kinetically coupled to drive wheel 36 via a belt 54. As an alternative to the configuration shown in FIG. 4, shaft 52 may also be kinetically coupled with drive wheel 36 via a toothed wheel connection.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A swiveling device for a swiveling C-arm (8) of an X-ray unit, the swiveling device comprising:
    a motorized drive unit (24);
    an adapter (20) removably attachable to the C-arm (8) concentrically with a swiveling axis (A) thereof, via which the C-arm (8) connects to the drive unit (24) in a driving manner, and to an angular position encoder (50) for recording the swivel angle of the C-arm (8); and
    a friction clutch arranged between a drive motor of the drive unit (24) and the adapter (20), wherein a part of the drive unit (24) connected to the adapter (20) forms a part of the friction clutch.

2. The swiveling device according to claim 1, wherein the angular position encoder (50) is arranged for recording the swivel angle of a part of the drive unit (24) connected with the adapter (20).

3. The swiveling device according to claim 2, wherein the angular position encoder (50) is a potentiometer (50), whose slider is kinetically coupled to the part of the drive unit (24) connected to the adapter (20) via a toothed belt drive.

4. The swiveling device according to claim 3, in which the slider of the potentiometer (50) is kinetically coupled to the part of the drive unit (24) connected to the adapter (20) via a toothed wheel connection.

5. The swiveling device according to claim 1, wherein a drive shaft (34) of an electric motor (32) is kinetically coupled to the part of the drive unit (24) connected to the adapter (20) via a worm drive.

6. The swiveling device according to claim 1, wherein a part of the drive unit (24) connected to the adapter (20) has positive locking elements that are provided to engage with corresponding positive locking elements on the adapter (20).

7. The swiveling device according to claim 1, wherein the drive unit (24) is arranged on a pivot arm (26) that is secured to the X-ray unit.

8. The swiveling device according to claim 1, wherein the adapter (20) is secured on the C-arm (8) by means of a clamping device.

9. The swiveling device as recited in claim 8, wherein the adapter is arranged on a clip that is open on one side, and the clip is clamped to the C-arm of an X-ray unit.

* * * * *